United States Patent [19]

Tagami

[11] Patent Number: Plant 7,441

[45] Date of Patent: Feb. 5, 1991

[54] ANTHURIUM PLANT NAMED PINK ARISTOCRAT

[75] Inventor: Hiroshi Tagami, Kaneohe, Hi.

[73] Assignee: Hartman Plant Laboratories, Inc., Sebring, Fla.

[21] Appl. No.: 454,741

[22] Filed: Dec. 21, 1989

[51] Int. Cl.[5] ..... A01H 5/00

[52] U.S. Cl. ..... Plt./88

[58] Field of Search ..... Plt./88

*Primary Examiner*—Howard J. Locker

*Attorney, Agent, or Firm*—Foley & Lardner, Schwartz, Jeffery, Schwaab, Mack, Blumenthal & Evans

[57] ABSTRACT

An Anthurium plant named Pink Aristocrat having flowers which change from pink to cream and then to green as they age, symmetrical habit with free branching, long lasting flowers which are held well above the leaf canopy, axillary shoots that bloom from the first expanded leaf, and durable dark green leaves with good texture and a shiny surface.

2 Drawing Sheets

The present invention comprises a new and distinct cultivar of Anthurium, botanically known as *Anthurium andraeanum*, and referred to by the cultivar name Pink Aristocrat.

The new cultivar is a product of a planned breeding program carried out by the inventor Hiroshi Tagami, Kaneohi, Hi. The seedling is a result of an unknown cross made in Kaneohe, Hi. The cultivar was discovered from the progeny of the stated cross by Hiroshi Tagami. Propagation by division was used to increase the number of plants for evaluation and has demonstrated the stability of the combination of characteristics from generation to generation.

The following observations, measurements and values describe plants grown in Palmdale, Fla. and Kaneohe, Hi. under greenhouse conditions which closely approximate those generally used in horticultural practice.

The following traits have been repeatedly observed to be characteristics which in combination distinguish Pink Aristocrat from other Anthurium of the same general type, for example, the well known cultivar Lady Jane.

1. A flower can last as long as one year.
2. The flowers change from pink to cream and then to green as they age.
3. The flowers are held well above the leaf canopy.
4. On a mature plant, the axillary shoots can bloom from the first expanded leaf.
5. The leaves have good texture, are dark green, have a shiny surface, and are durable.
6. The plant habit is symmetrical with good height and width.
7. The plant is free branching.
8. The plant is heat tolerant.
9. The plant exhibits brighter flower colors under growing conditions in Hawaii.

All color references are measured against The Royal Horticultural Society colour chart. Colors are approximate as color depends on horticultural practices such as light level and fertilization rate, among others.

The drawings comprise color photographs, with Sheet 1 being a top perspective view of the inflorescence and foliage of Pink Aristocrat, and Sheet 2 comprising a closeup view of the inflorescence. The photograph comprising sheet 1 is a plant of Pink Aristocrat in a 19.8 cm pot approximately 45–50 weeks after planting a cutting obtainable by division, and grown under approximate growing conditions. Colors are as accurate as possible with color illustrations of this type. It is noted that the illustrated spathe color is more reddish than the color values indicated below, which are correct.

Origin: Seedling of unknown parentage.

Classification: *Anthurium andreaeanum*, cv. Pink Aristocrat.

Propagation: Asexual production either by tissue culture or division.

Plant: In a 19.8 cm. pot for a plant grown from division after 45–50 weeks under appropriate growing conditions, Pink Aristocrat will be at the mature size of approximately 33 cm. to 45 cm. in height and approximately 70 cm. to 80 cm. in width.

Leaves:

*Form.*—The leaf blade is ovate with an acuminate tip and a truncate base. The margins are entire. The midrib tends to curve over the length of the leaf. The leaf blade tends to be straight over the width of the leaf.

*Size.*—Leaf blades of a mature sized plant will be approximately 20 cm. to 23 cm. in length and approximately 12 cm. to 14 cm. in width.

*Petiole.*—The petiole is approximately 20 cm. to 26 cm. in height from the base of the petiole to the base of the leaf blade on the primary shoot. Secondary shoots are somewhat smaller depending on the age of the shoot. The petiole will be approximately 3.5 mm. to 4.5 mm. in diameter just below the geniculum. The petiole below the geniculum will be curved.

*Petiole wings.*—Petiole wings will be approximately 3.8 cm. to 4.2 cm. in length and approximately 3 mm. to 4 mm. in width at their midpoint. The tip of the petiole wings will be acute. There is approximately 17 cm. to 19 cm. between the top of the wing and the base of the geniculum.

*Geniculum.*—The geniculum is approximately 23 mm. to 28 mm. in length and approximately 4.5 mm to 5.5 mm. in diameter, and is curved. The color is 46B. There is no space between the top of the geniculum and the base of the leaf blade. The geniculum is prominent.

*Veins.*—Veins are sunken, with the leaf blade slightly convex between veins on the upper surface. Well defined primary veins on leaves radiate out from the juncture of the petiole and the leaf. Veins stand out prominently on the lower side. There are approximately 6 primary veins on the leaf.

*Lobes.*—The leaf has two lobes extending past the petiole. The distance from the petiole/leaf juncture to the highest point on the lobes will be approximately 3.5 cm. to 4.5 cm.

*Color.*—Upper surface: 137A. Lower surface: 134C-D, 143C-D. Midrib, upper surface: 144A. Midrib, lower surface: 144D, 145B. Petiole: 46B. Petiole wing: 144B.

Inflorescence:

*Immature.*—The spathe is tightly rolled around the spadix and extrudes from the petiole sheath. The spathe is fully open approximately when the pedicel is fully elongated — approximately 35 cm. to 45 cm. above the soil surface.

*Mature.*—Spathe: Size: The flattened spathe is approximately 8 cm. to 9 cm. long and approximately 6 cm. to 7 cm. in width. Color: Florida: Fully open: Upper surface: 50B. Lower surface: 47B, 47D. Faded: Upper surface: 19D with some residual pink. Lower surface: 48D with spots of green; veins are 19D. Hawaii: Fully open: Upper surface: 50A, 51A. Lower surface: 47A, 47C. Faded: Upper surface: 19D with some residual pink. Lower surface: 51A with spots of green; veins are 19D. Arrangement: The spathe stands up on straight wiry pedicels and opens vertically above the leaves. Shape: The spathe is ovate with a cuspidate apice that is straight. It is slightly cupped when first open and is approximately 7 cm. to 8 cm. in height and approximately 6 cm. to 7 cm. in width. It is approximately 1 cm. in depth. The spathe flattens and reflexes as it ages. Flowering time: After approximately 11-12 months for an untreated plant depending on season, approximately 5 to 8 blossoms will be present. Smaller blossoms may occur on less mature growth.

Reproductive organs:

*Spadix.*—Size: Approximately 4.5 cm. to 5.5 cm. in height and approximately 6 mm. to 7 mm. in width. Color: Florida: When the spathe unrolls, the spadix is 54D, gradually changing to 146C before senescing. Hawaii: When the spathe unrolls, the spadix is 54C, gradually changing to 152A before senescing. Stamens: Anthers and filaments are not clearly visible. Pollen: White in color. Pistil: Lighter than 54D in color, protruding between the staminate flowers, firmly fixed to the main axil. The pistilate flowers extend approximately 0.5 mm to 1.0 mm. beyond the staminate flowers.

Roots: White fleshy roots with fine laterals.

General observation: Pink Aristocrat has long lived pink flowers that change to a cream color and then green as they age. The plant is free blooming and can bloom on axillary shoots that have only one leaf expanded. Compared to other Anthuriums of this type (Lady Jane), there are numerous axillary shoots. The leaves are a dark green and are extremely durable. The plant habit is symmetrical. Pink Aristocrat is heat tolerant and has brighter flowers when grown under Hawaiian conditions. Pink Aristocrat is a unique new cultivar.

I claim:

1. A new and distinct cultivar of Anthurium plant named Pink Aristocrat, as illustrated and described.

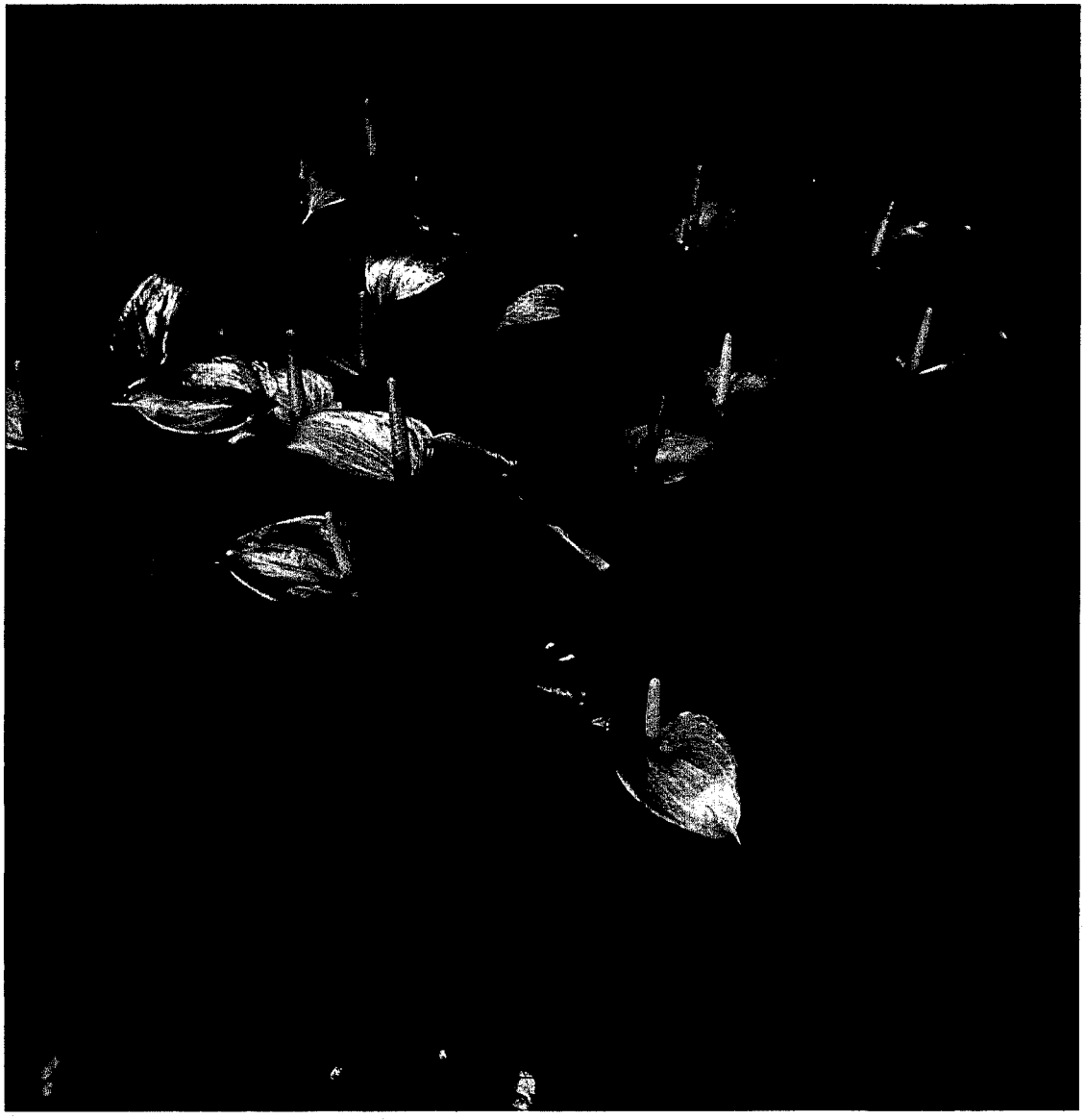

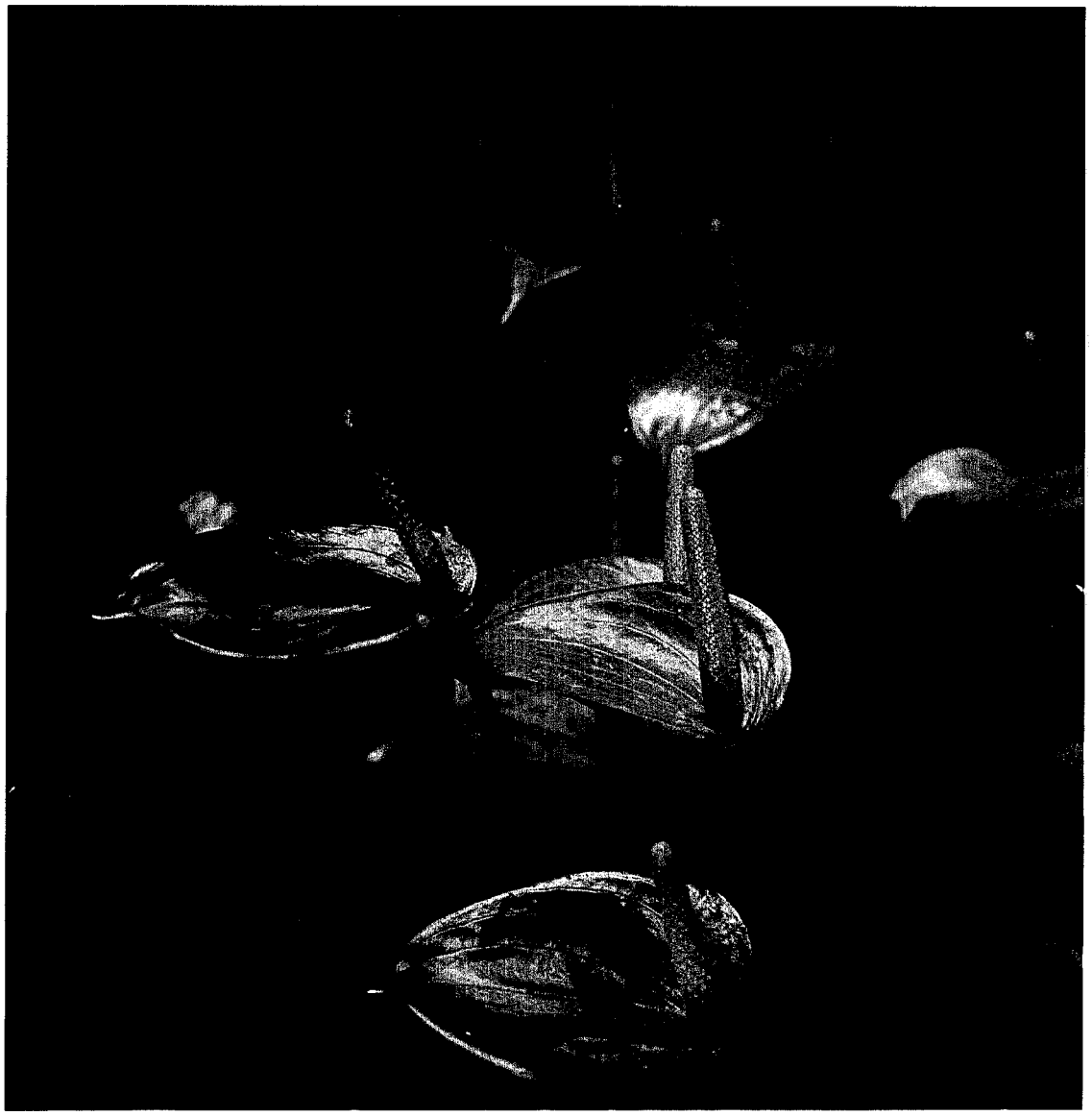

* * * * *